(12) United States Patent
Benson

(10) Patent No.: US 10,806,646 B2
(45) Date of Patent: Oct. 20, 2020

(54) SPINAL IMMOBILIZATION DEVICE, SYSTEM, AND METHOD OF USE

(71) Applicant: Robin Benson, Las Cruces, NM (US)

(72) Inventor: Robin Benson, Las Cruces, NM (US)

(*) Notice: Subject to any disclaimer, the term of this patent is extended or adjusted under 35 U.S.C. 154(b) by 0 days.

(21) Appl. No.: 16/496,299

(22) PCT Filed: May 28, 2019

(86) PCT No.: PCT/US2019/034182
§ 371 (c)(1),
(2) Date: Sep. 20, 2019

(87) PCT Pub. No.: WO2019/236337
PCT Pub. Date: Dec. 12, 2019

(65) Prior Publication Data
US 2020/0276064 A1   Sep. 3, 2020

Related U.S. Application Data

(60) Provisional application No. 62/681,281, filed on Jun. 6, 2018, provisional application No. 62/771,938, filed on Nov. 27, 2018.

(51) Int. Cl.
*A61G 1/04* (2006.01)
*A61G 1/00* (2006.01)
*A47C 27/08* (2006.01)

(52) U.S. Cl.
CPC .............. *A61G 1/04* (2013.01); *A47C 27/085* (2013.01); *A47C 27/086* (2013.01); *A61G 1/00* (2013.01)

(58) Field of Classification Search
CPC . A61G 1/00; A61G 1/013; A61G 1/04; A61G 1/044; A61G 1/048; A61G 13/12; A61G 13/1205; A61G 13/121; A61G 13/122; A61G 13/1225; A47C 27/08; A47C 27/081; A47C 27/085; A47C 27/086
USPC ........ 5/625–629, 654, 644, 655.4, 702, 911; 128/845, 846, 869, 870
See application file for complete search history.

(56) References Cited

U.S. PATENT DOCUMENTS

| | | | | |
|---|---|---|---|---|
| 3,775,782 A | * | 12/1973 | Rice ......................... | A61G 1/00 5/625 |
| RE28,916 E | * | 7/1976 | Rice ......................... | A61G 1/00 5/628 |
| 4,261,349 A | | 4/1981 | Lambson et al. | |
| 4,301,791 A | * | 11/1981 | Franco, III ............... | A61G 1/00 602/19 |

(Continued)

OTHER PUBLICATIONS

International Search Report and Written Opinion, PCT/US2019/034182, dated Aug. 9, 2019.

*Primary Examiner* — Robert G Santos
(74) *Attorney, Agent, or Firm* — Polsinelli PC

(57) ABSTRACT

A spinal immobilization device including a base member and a spinal support member configured to overlay the base member. The base member includes an elongate board having a curvate top surface, a plurality of openings surrounding at least a portion of the elongate board, and a channel defined within the top surface. The spinal support member may include a bladder, a valve controlling passage of fluid into the bladder, and a plurality of fluid absorbing members within the bladder. The channel defines an impression within the top surface that matches a shape of a portion of the bladder.

11 Claims, 10 Drawing Sheets

(56) References Cited

U.S. PATENT DOCUMENTS

| | | | |
|---|---|---|---|
| 4,370,768 A * | 2/1983 | Saloff | A47C 27/088 156/145 |
| 4,466,145 A * | 8/1984 | Jones | A61G 1/00 441/40 |
| 4,612,678 A * | 9/1986 | Fitsch | A61G 1/04 128/870 |
| 4,621,382 A * | 11/1986 | Burriss | B63C 9/08 441/129 |
| 4,736,474 A | 4/1988 | Moran et al. | |
| 4,840,362 A * | 6/1989 | Bremer | A61G 13/12 5/621 |
| 4,895,173 A * | 1/1990 | Brault | A61G 1/01 128/870 |
| 4,942,634 A * | 7/1990 | Saloff | A47C 27/085 5/682 |
| 4,979,520 A * | 12/1990 | Boone, Jr. | A61G 1/01 128/870 |
| 4,980,939 A * | 1/1991 | Smith | A47C 7/021 190/1 |
| 5,088,137 A * | 2/1992 | Rose | A61G 1/04 128/870 |
| 5,113,540 A * | 5/1992 | Sereboff | A47C 7/021 297/452.41 |
| 5,121,756 A | 6/1992 | Koledin | |
| 5,154,185 A * | 10/1992 | Latimer | A61F 5/05833 128/DIG. 20 |
| 5,195,199 A * | 3/1993 | Sereboff | A47C 7/021 5/654 |
| 5,317,770 A | 6/1994 | Sakurai | |
| 5,560,059 A * | 10/1996 | McQueen | A61G 1/00 128/870 |
| 5,568,662 A * | 10/1996 | Gougelet | A61F 5/05883 128/870 |
| 5,626,150 A | 5/1997 | Johnson et al. | |
| 5,819,746 A * | 10/1998 | Walton | A61G 1/00 128/869 |
| 5,826,583 A * | 10/1998 | Wood | A61G 7/05753 128/869 |
| 6,061,853 A * | 5/2000 | Laaksonen | A61G 1/007 5/625 |
| 6,065,165 A * | 5/2000 | Delk | A61G 1/01 5/625 |
| 6,138,306 A * | 10/2000 | Muhanna | A61G 1/00 128/870 |
| 6,425,399 B1 * | 7/2002 | Hoster, Jr. | A61F 5/05816 128/869 |
| 6,848,134 B1 * | 2/2005 | Schenck | A61G 1/04 128/870 |
| 6,915,805 B2 * | 7/2005 | Crutchfield | A61G 1/00 128/870 |
| 6,964,073 B1 * | 11/2005 | Curry | A61G 1/00 128/870 |
| 7,028,357 B2 * | 4/2006 | Holland | A61G 1/00 128/870 |
| 7,055,199 B2 * | 6/2006 | Thompson | A47C 7/467 5/626 |
| 7,100,226 B1 * | 9/2006 | Walton | A61G 1/00 128/870 |
| 7,120,950 B2 * | 10/2006 | Garrigues | A47C 27/088 5/420 |
| 7,228,579 B2 * | 6/2007 | Tidwell | A61B 6/0421 378/209 |
| 7,437,789 B2 * | 10/2008 | Thompson | A47C 7/467 5/626 |
| 7,707,667 B1 * | 5/2010 | Walton | A61G 1/04 128/870 |
| 8,096,008 B1 * | 1/2012 | Phillips | A61G 1/013 128/870 |
| 8,240,310 B2 | 8/2012 | Soung | |
| 8,328,592 B2 * | 12/2012 | Cynamon | B63C 9/04 441/40 |
| 8,365,326 B2 * | 2/2013 | Kenalty | A61G 1/00 5/625 |
| 8,469,911 B2 | 6/2013 | Hiebert | |
| 8,881,327 B2 * | 11/2014 | Kenalty | A61G 1/00 5/625 |
| 9,084,702 B2 * | 7/2015 | Bertsch | A61G 1/013 |
| 9,205,007 B2 * | 12/2015 | Chinn | A61G 1/048 |
| 9,445,933 B2 | 9/2016 | Williams | |
| 9,763,838 B2 * | 9/2017 | Piccolo-Wignall | A61G 1/04 |
| 9,861,539 B1 | 1/2018 | Stickler et al. | |
| 2003/0200972 A1 * | 10/2003 | Crutchfield | A61G 1/00 128/845 |
| 2004/0187214 A1 * | 9/2004 | Holland | A61M 5/1415 5/626 |
| 2004/0211004 A1 * | 10/2004 | Thompson | A47C 7/467 5/655.3 |
| 2005/0166325 A1 * | 8/2005 | Tidwell | A61B 6/0485 5/624 |
| 2006/0016003 A1 * | 1/2006 | Garrigues | A47C 27/088 5/420 |
| 2007/0039102 A1 | 2/2007 | Thompson | |
| 2009/0000027 A1 | 1/2009 | Jarrett, III | |
| 2010/0233922 A1 * | 9/2010 | Cynamon | B63C 9/04 441/80 |
| 2011/0120478 A1 | 5/2011 | Thompson et al. | |
| 2011/0185504 A1 * | 8/2011 | Kenalty | A61G 1/044 5/626 |
| 2012/0180218 A1 * | 7/2012 | Augustijn | A61G 1/007 5/626 |
| 2012/0284923 A1 * | 11/2012 | Jensen | A61G 1/04 5/627 |
| 2013/0139319 A1 * | 6/2013 | Kenalty | A61G 1/00 5/628 |
| 2013/0340170 A1 * | 12/2013 | Chinn | A61G 1/04 5/628 |
| 2014/0082844 A1 * | 3/2014 | Bertsch | F41H 5/08 5/627 |
| 2016/0008190 A1 * | 1/2016 | Piccolo-Wignall | A61G 1/044 128/870 |
| 2016/0067126 A1 | 3/2016 | Purdy et al. | |
| 2017/0246041 A1 | 8/2017 | Cumming et al. | |

* cited by examiner

SPINAL IMMOBILIZATION DEVICE, SYSTEM, AND METHOD OF USE

CROSS-REFERENCE TO RELATED APPLICATIONS

The present application claims the benefit of U.S. Provisional Patent Application No. 62/681,281, filed Jun. 6, 2018, entitled "TRUESPINE SPINAL IMMOBILIZATION DEVICE, SYSTEM, AND METHOD," which is hereby incorporated by reference in its entirety into the present application. The present application also claims the benefit of U.S. Provisional Patent Application No. 62/771,938, filed Nov. 27, 2018, entitled "SPINAL IMMOBILIZATION DEVICE, SYSTEM, AND METHOD OF USE," which is hereby incorporated by reference in its entirety into the present application.

TECHNICAL FIELD

The present disclosure relates to spinal immobilization devices, systems, and methods. More specifically, the present disclosure relates to spinal immobilization devices, systems, and methods utilizing a spinal board having a base and an expandable overlay.

BACKGROUND

Prehospital spinal immobilization has long been the standard of care to prevent spinal cord injury in trauma patients. However, rigid spinal immobilization using a long spinal board or backboard may present risks to patients with a possible spinal injury that can often lead to greater injury if not immobilized properly. Patients may be evaluated on scene of an accident by an Emergency Medical Technician (EMT) or paramedic to determine whether spinal immobilization is needed. A variety of protocols for backboarding often leads to confusing and inconsistent practices between EMT units in different locations across the United States.

The 2013 report from the National Association of EMS Physicians and the American College of Surgeons Committee on Trauma addressed improper use of the long backboard for spinal immobilization. Improper use can lead to moderate to severe pain, decreased forced vital capacity in the adult and pediatric populations, compromised vascular function, and increased risk of pressure ulcers, and disrupting an emergency department's assessment of traumatic injuries. In short, immobilizing using a long backboard often causes greater injury than the initial injury. Guidelines released in 2014 from the National Association of EMS Physicians (NAEMSP) and the American College of Surgeons Committee on Trauma (ACS-COT) support limited application of spinal immobilization with conventional backboards. The Guidelines conclude, "[u]tilization of backboards for spinal immobilization during transport should be judicious, so that potential benefits outweigh risks."

Accordingly, the device, system, and method disclosed herein are intended to provide a useful and beneficial alternative to using conventional long spinal boards when immobilizing patients.

SUMMARY

Aspects of the present disclosure may involve a spinal immobilization including a base member and a spinal support member configured to overlay the base member. The base member includes an elongate board having a curvate top surface, a plurality of openings surrounding at least a portion of the elongate board, and a channel defined within the top surface. The spinal support member may include a bladder, a valve controlling passage of fluid into the bladder, and a plurality of fluid absorbing members within the bladder. The channel defines an impression within the top surface that matches a shape of a portion of the bladder.

In certain instances, the bladder may include a head support portion and a spinal support portion, and the channel may include a head support portion and a spinal support portion, the head support portion and the spinal support portion of the bladder configured to partially inlay within the head support portion and the spinal support portion of the channel, respectively.

In certain instances, the spinal support portion of the bladder may include a pair of tubular structures, and the head support portion of the bladder may include a semi-circular tubular structure that interconnects the pair of tubular structures at an end thereof.

In certain instances, the bladder further may include a plurality of tubular support structures coupled between the pair of tubular structures.

In certain instances, the elongate board further may include a planar bottom surface opposite the top surface.

In certain instances, the impression may be semi-cylindrical.

In certain instances, the plurality of openings defines handle of the spinal board.

In certain instances, the base member may be of a unitary construction.

In certain instances, the base member may be formed of a polymer.

In certain instances, the plurality of fluid absorbing members expand upon the introduction of saline into the bladder.

In certain instances, the device may include a double-sided adhesive adhered to the bladder on one side of the double-sided adhesive.

In certain instances, the device may include straps for coupling to the plurality of openings and extending across the base member.

In certain instances, the at least one valve may include two valves positioned at a head support portion of the bladder.

In certain instances, in the spinal support member further may include at least one baffle positioned within the bladder to restrain movement of the plurality of fluid absorbing members within the bladder.

In certain instances, the at least one baffle permits fluid to pass there through.

Aspects of the present disclosure may involve a method of immobilizing a spine of a patient having a head. The method may include applying a spinal support member of a spinal immobilization device to the spine of the patient, the spinal support member may include a bladder, at least one valve controlling passage of fluid into and out of the bladder, and a plurality of fluid absorbing members within the bladder, the bladder being uninflated when the spinal support member may be applied to the spine of the patient. The method may also include injecting a fluid into the bladder of the spinal support member through the at least one valve, thereby causing the plurality of fluid absorbing members to expand whereby inflating the bladder. The method may also include positioning the patient on a base member of the spinal immobilization device such that the spinal support member fit within channels formed in a top surface of the base member.

In certain instances, applying the spinal support member to the spine of the patient may include taping the spinal support member to the spine of the patient.

In certain instances, the spinal support member may include a semi-circular head support portion coupled to a pair of longitudinal support members, the semi-circular head support portion configured to support the head of the patient, the pair of longitudinal support members configured to support sides of the spine of the patient.

In certain instances, the device may include removing the spinal support member from packaging prior to applying the spinal support member to the spine of the patient.

In certain instances, the device may include transferring the patient on the base member to a stretcher.

DETAILED DESCRIPTION

Figure 1:
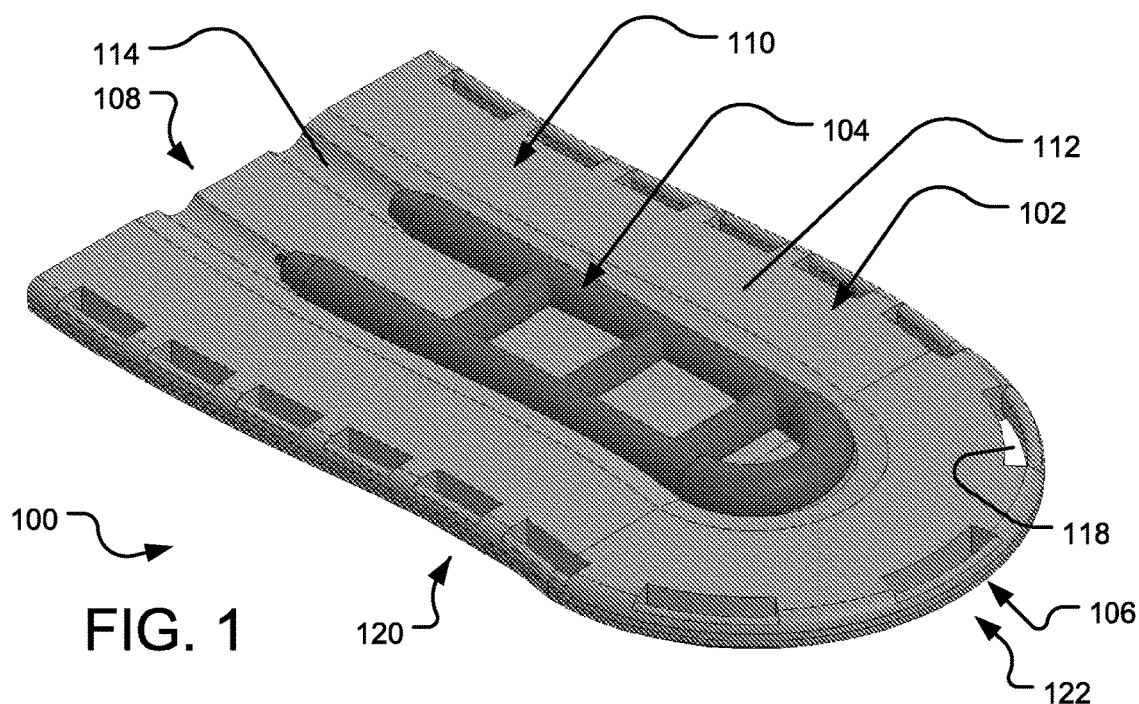
FIG. 1 is an isometric top view of a spinal board as viewed from the head end.
Figure 2:
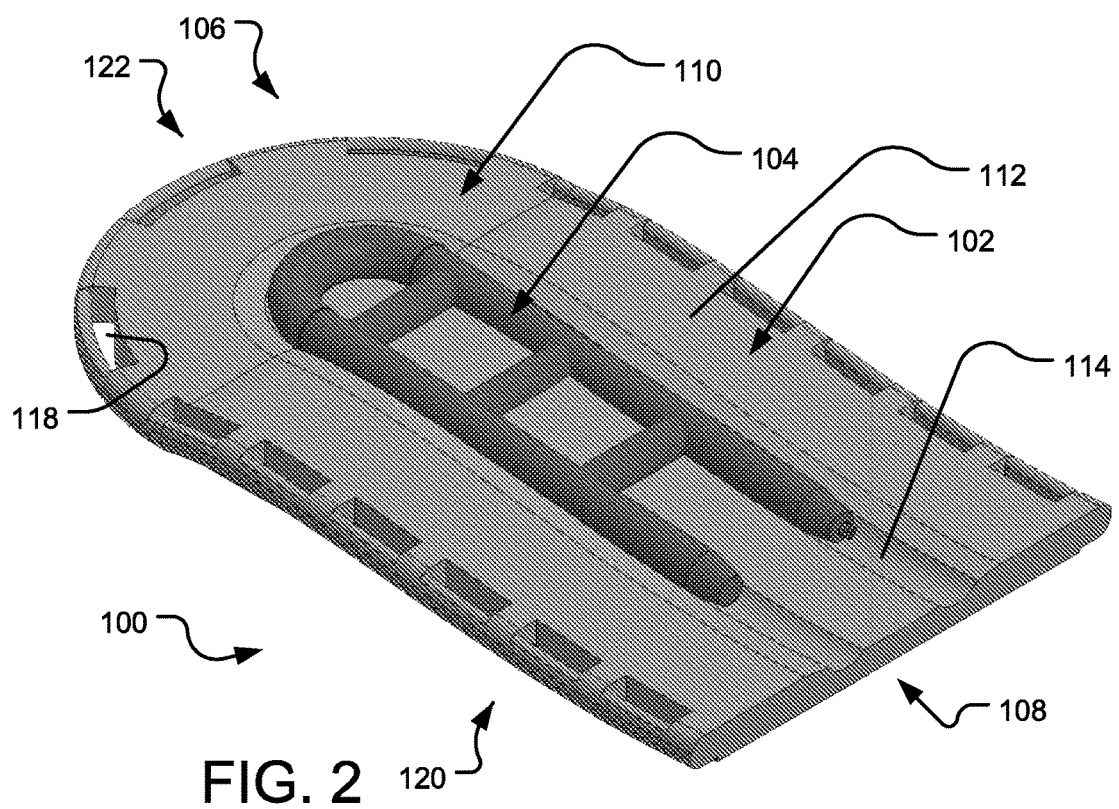
FIG. 2 is an isometric top view of the spinal board as viewed from the foot end.

Referring to FIGS. 1 and 2, which are, respectively, isometric top views of a spinal board, spinal immobilization device, or spinal immobilizer 100 from a head end 106 and a foot end 108, the spinal immobilization device 100 may include a base member 102 and a spinal support member 104 (also called an overlay or inlay) overlaid on the base member 102. The spinal immobilization device 100 as described herein may be used to immobilize a patient's spine along with straps (not shown in the drawings). In certain instances, the spinal immobilization device 100 may be used by in place of a traditional long spinal board, cot, gurney, or stretcher. That is, the spinal immobilization device 100 may be employed to immobilize and transport a patient having a spinal condition. In certain instances, the spinal immobilization device 100 may be used in conjunction with a traditional long spinal board, cot, gurney, or stretcher. That is, a patient may be initially immobilized by being safely and securely immobilized with the spinal immobilization device 100, and a medical worker(s) may place the immobilized patient and spinal immobilization device 100 onto a traditional long spinal board, cot, gurney, or stretcher for transportation.

Figure 3:
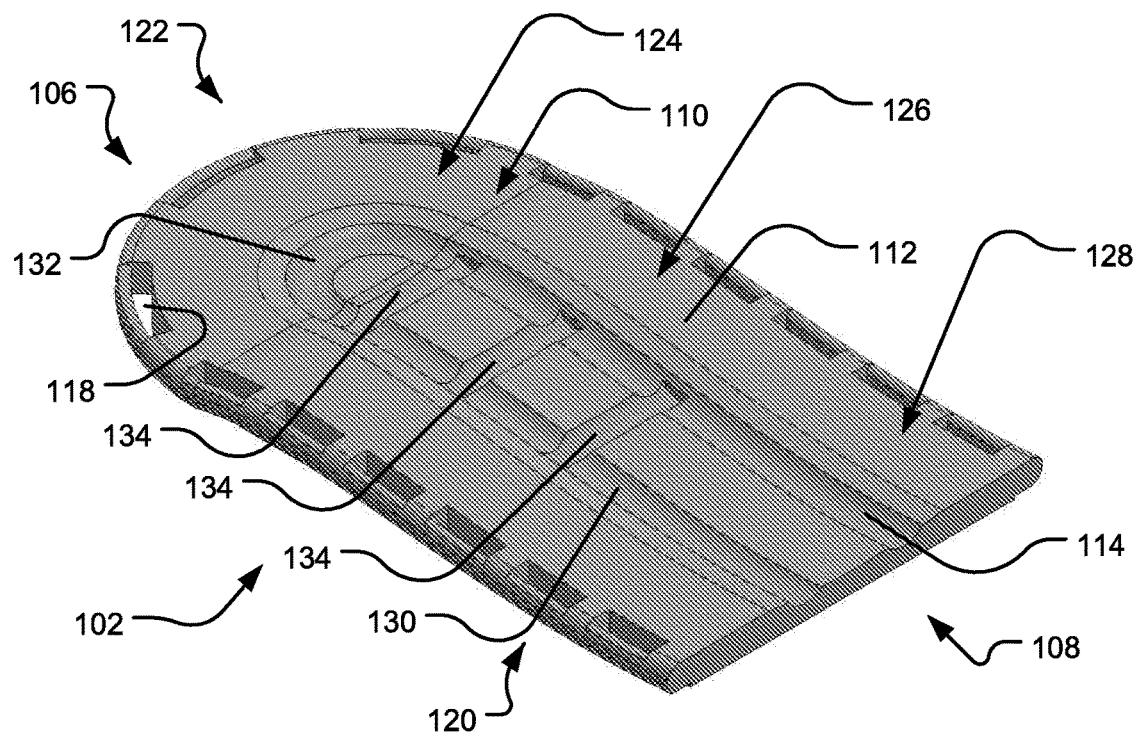
FIG. 3 is an isometric top view of a base member of the spinal board as viewed from the foot end.
Figure 4:
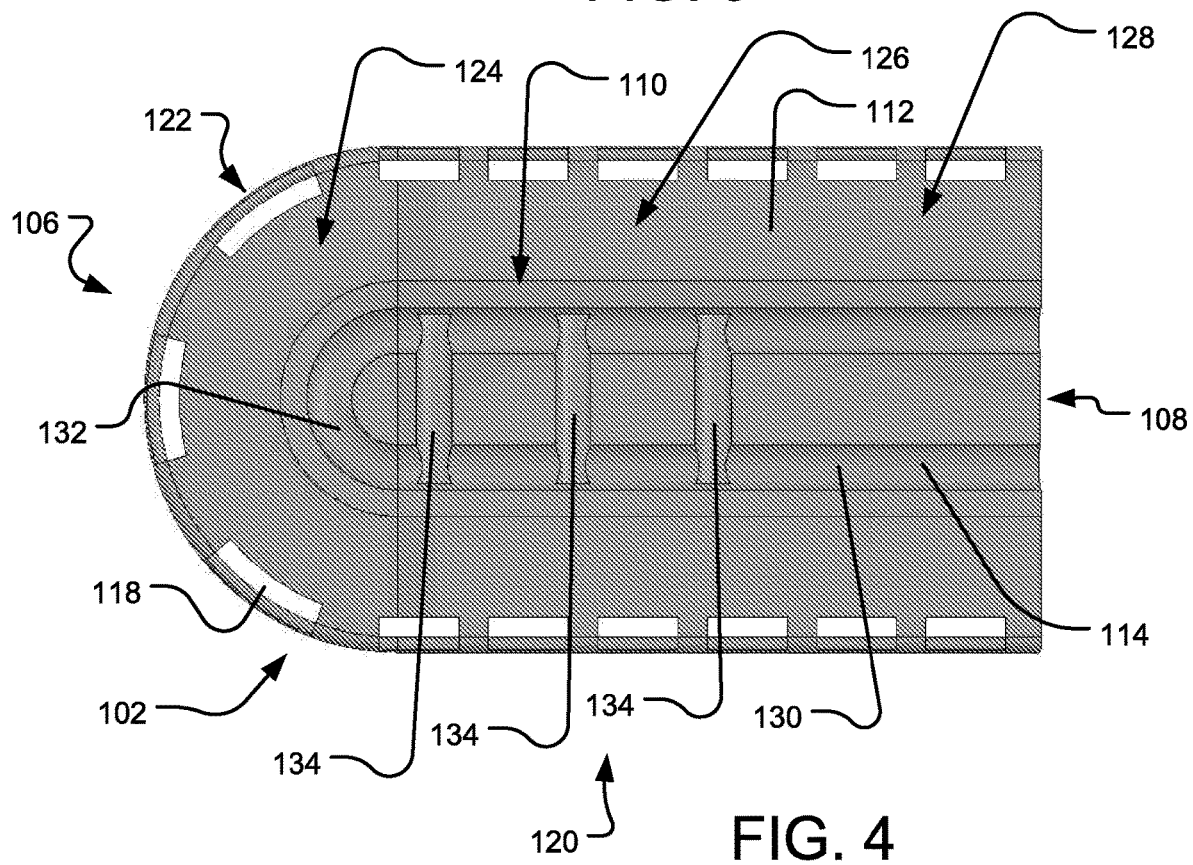
FIG. 4 is a top view of the base member.
Figure 5:
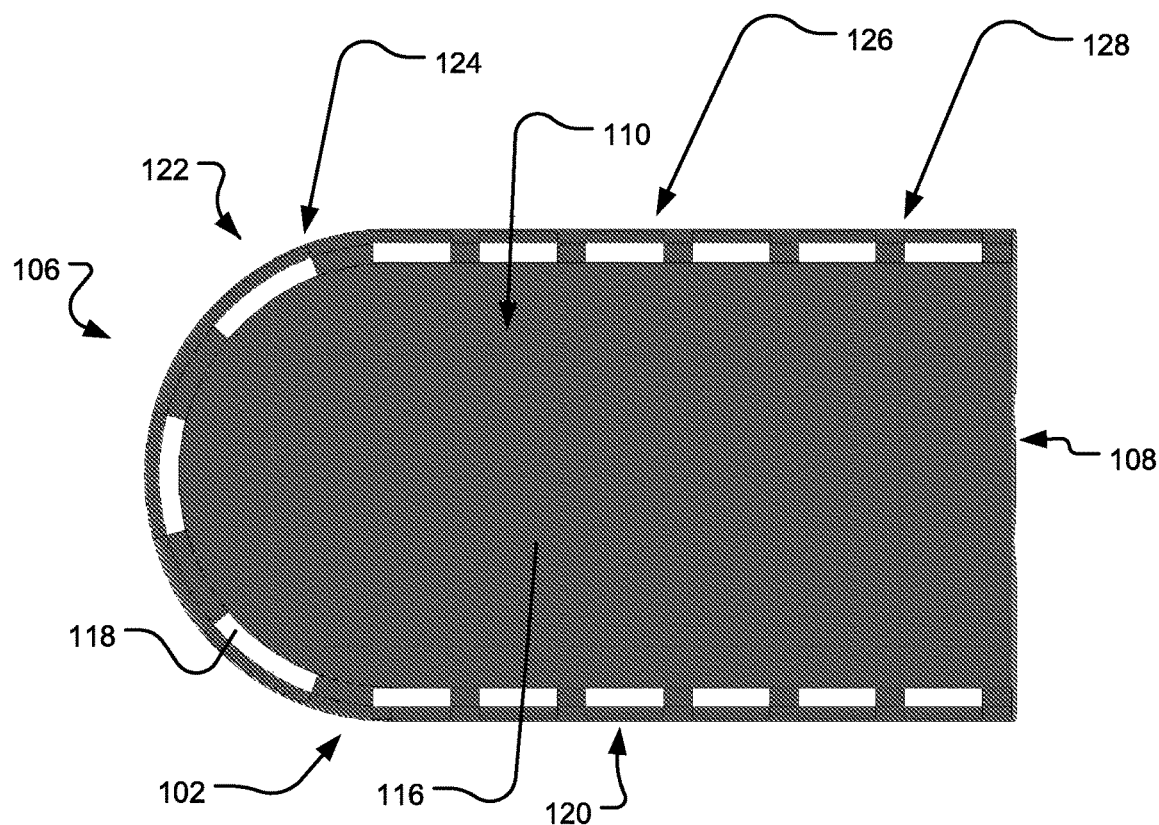
FIG. 5 is bottom view of the base member.
Figure 6:
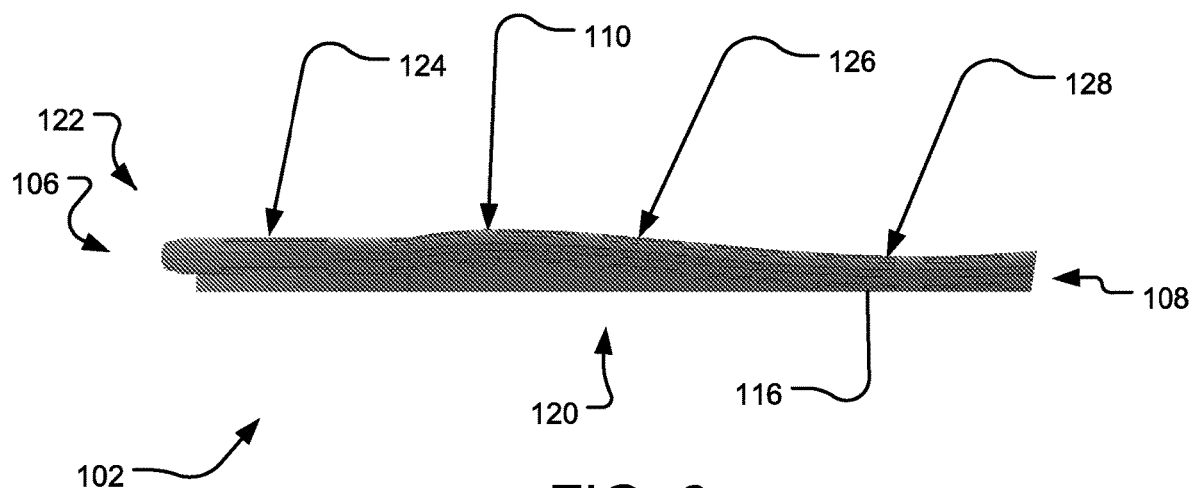
FIG. 6 is a side view of the base member.

The base member 102 as seen in FIGS. 1-2, as well as FIGS. 3-4, which are, respectively, an isometric top view and a top view of the base member 102, it may include an elongate board 110 having a curvate top surface 112 and a channel 114 defined within a central portion of the board 110. As seen in FIGS. 5-6, which are, respectively, a bottom view and a side view of the base member 102, it may include a planar bottom surface 116, and openings 118 around a periphery of the longitudinal sides 120 and the rounded head end side 122 of the board 110. The openings 118 define handles for users (e.g., EMT) to grasp when lifting or otherwise moving the spinal immobilization device 100.

The base member 102 of the spinal immobilization device 100 may be manufactured or otherwise constructed or formed from a single material. That is, the base member 102 may be unitarily constructed from, for example, a polymer material such as ABS, PEEK, PAEK (polyaryletherketone), Kydex, or the like. In certain instances, the base member 102 may be constructed of multiple materials. That is, in certain instances, the base member 102 may be non-monolithic or a composite of more than one material.

Dimensions of the base member 102 of the spinal immobilization device 100 may be as follows. In certain instances, the length of the base member from the head end 106 to the foot end 108 may be about three feet. In certain instances, the length of the base member from the head end 106 to the foot end 108 may be about four feet. In certain instances, the length of the base member from the head end 106 to the foot end 108 may be about five feet. In certain instances, the width of the base member from opposite sides 120 may be about two feet. In certain instances, the width of the base member from opposite sides 120 may be about three feet.

As particularly seen in FIGS. 3 and 6, the base member 102 may include a head section 124, a midsection 126, and a lower body section 128. As seen in the figures, the midsection 126 is raised compared to the head section 124 and the lower body section 128. The curvature of the top surface 112 mimics the contours of a patient's spine so as to be a more natural support surface for patient supported thereon.

As seen in FIG. 3, the channel 114 may define a semi-cylindrical cross-sectional indentation or impression within the top surface 112. The channel 114 may include a pair of spinal support sections 130, a head support section 132 that is rounded and that connects the pair of spinal support sections 130, and a series of transverse sections 134 connected between the pair spinal support sections 130. As seen in FIGS. 3-4, the pair of spinal support sections 130 are defined on the midsection 126 and foot section 128 of the base member 102, the transverse sections 134 are defined on the midsection 126 of the base member 102, and the head support section 132 is defined on the head section 124 of the base member 102.

Figure 7:
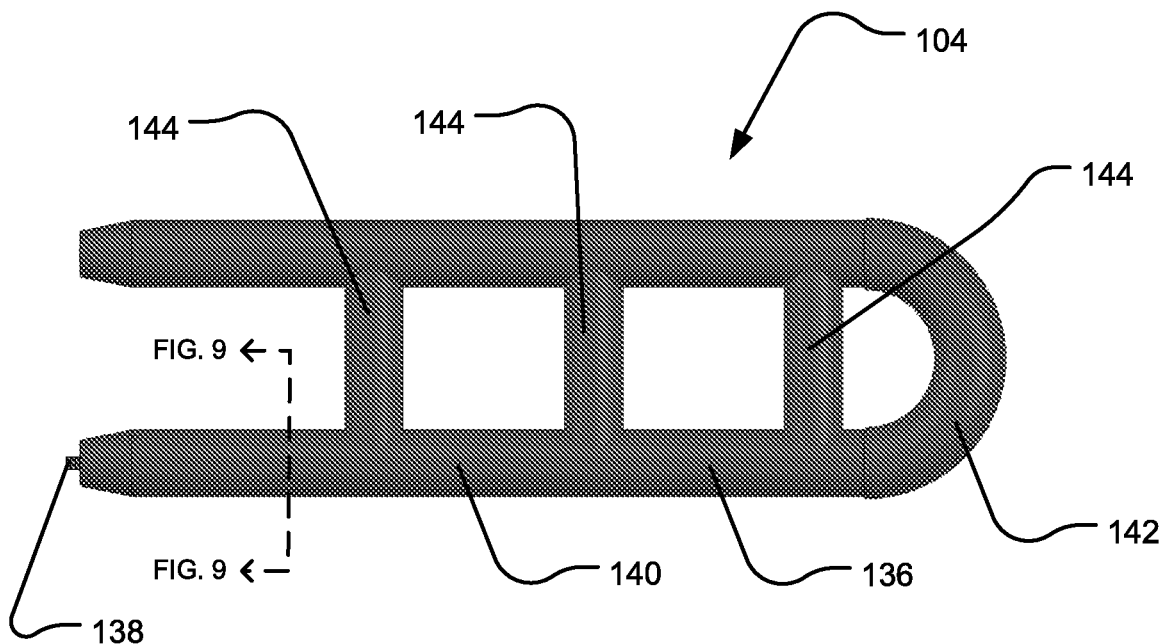
FIG. 7 is a top view of a spinal support member of the spinal board in an inflated or expanded state.
Figure 8:
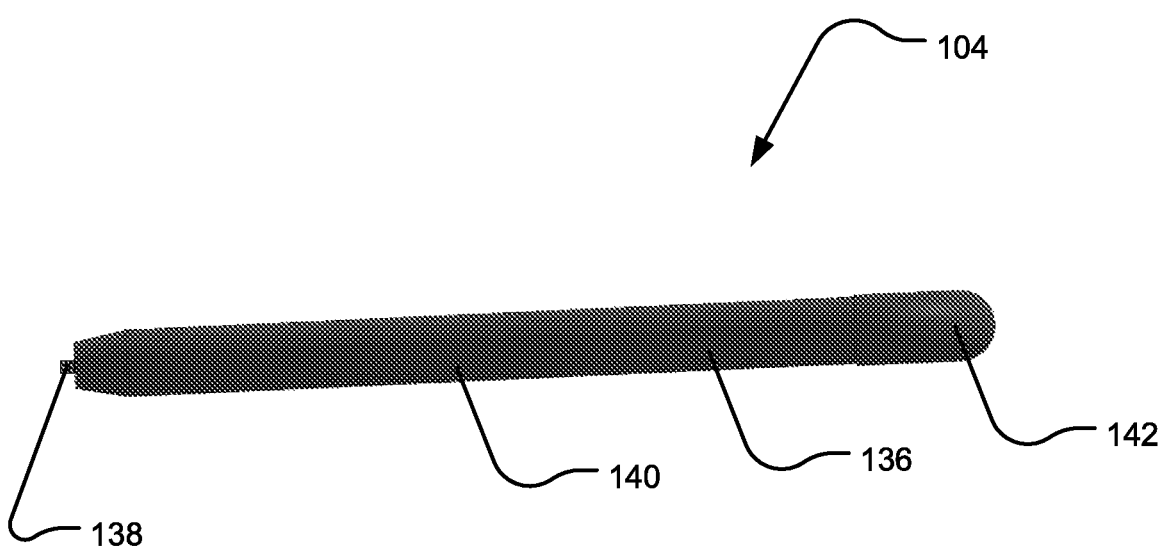
FIG. 8 is a side view of the spinal support member in a slightly inclined orientation (as it would be on supported on the base member) and in an inflated state.

Reference is now made to FIGS. 7 and 8, which are, respectively, top and side views of the spinal support member 104 of the spinal immobilization device 100 in an inflated or expanded state. The spinal support member 104 may be an enclosed tubular structure or bladder having an enclosed outer surface 136 (or bladder surface), which may be cylindrical and impermeable, and an orifice or valve 138 for controlling the passage of fluid into and out of the bladder. The spinal support member 104 may include a pair of longitudinal support members 140, a head support member 142 interconnecting ends of the pair of longitudinal support members 140, and a trio of transverse support members 144 interconnecting the longitudinal support members 140 along their length.

The head support member 142 is designed to cradle the superior portion of a patient's head, and may generally have a diameter of about 7 inches to about 8 inches (i.e., the diameter may be the distance between the longitudinal support members 140). The superior most transverse support member 144 is designed and positioned to support a patient's spine between C3 and C7, around the base of the neck that curves anteriorly. The second or intermediate transverse support member 144 is positioned to provide lumbar support between L1 and L5. And the inferior most transverse support member 144 is designed and positioned to extend across the patient's pelvic region, in particular near the coccyx. In certain instances, there may be multiple spinal support members 104 of different sizes to fit different sizes of patients. In certain instances, the spinal support member 104 may generally fit all patients.

The spinal support member 104, and in particular the outer surface or bladder 136 may be formed of a Thermo Plastic Urethane ("TPU") such as those manufactured by Seal Werks (www.sealwerks.com).

Figure 9:
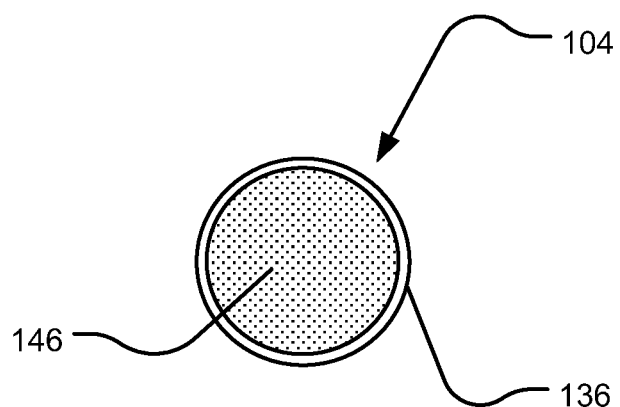
FIG. 9 is a cross-sectional view of the spinal support member enclosing the fluid absorbing members within the bladder of the spinal support member.

As seen in FIG. 9, which is a cross-sectional view of the spinal support member 104 in an expanded or inflated state, the outer surface 136 may enclose an amount of fluid absorbing particles or members 146 within the enclosed outer surface 136. The fluid absorbing particles 146 may absorb and expand upon the introduction of a fluid. In certain instances, the fluid absorbing particles 146 may be hydrogels, water-absorbing polymers, super-absorbent polymers (e.g., LiquiBlock™ 10G-270, 44-OC, 2G-110, 2G-70), absorbent laminates or composites, saline-absorbing polymers, or any known particle capable of absorbing and expanding upon the interaction with a fluid.

Figure 10:
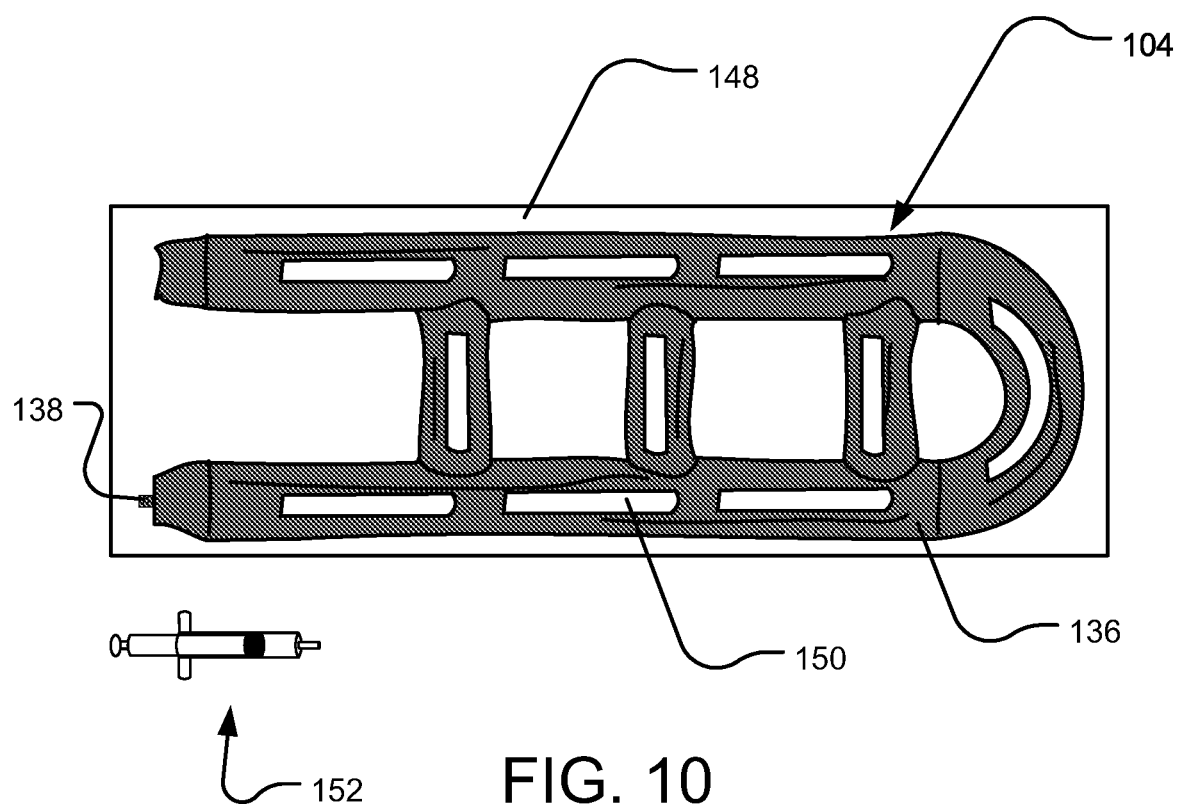
FIG. 10 is a top view of the spinal support member in a deflated state and enclosed within a sealed container or bag, along with a top view of a syringe.

Prior to the spinal support member 104 being in the expanded state, as shown in FIGS. 7-9, the spinal support member 104 may be in deflated state and enclosed within a wrapper, bag, or packaging 148, as seen in FIG. 10. The spinal support member 104 may include the amount of fluid absorbing particles 146 within the confines of the outer surface 136. But the fluid absorbing particles 146 are in a non-expanded or dry state at this time. As seen in FIG. 10, a double-sided adhesive 150 (e.g., 3M™ Tagaderm™) may be adhered to portions of the spinal support member 104. The double-sided adhesive 150 may be used to adhere to the patient's body prior to introducing a fluid into the spinal support member 104 so as to keep the patient and the spinal support member in a desirable position relative to each other. The packaging 148 encloses the spinal support member 104. The packaging 148 may include instructions on the packaging or within the wrapper of the packing 148. In certain instances, the spinal support member 104 may be a single use item. In certain instances, the spinal support member 104 may be used multiple times with appropriate cleaning and deflating (e.g., removal and replacement of the fluid absorbing particles 146).

To inflate the spinal support member 104, a syringe 152, as shown in FIG. 10, may be filled with a fluid (e.g., water, saline) designed to expand the fluid absorbing particles 146, and the syringe 152 may be inserted or otherwise engaged with the valve 138 of the spinal support member 104. The syringe 152 may be depressed so the fluid enters an inner volume of the enclosed outer surface 136 or bladder of the spinal support member 104. Once the fluid is within the enclosed outer surface 136, the fluid will contact the fluid absorbing particles 146 and cause the particles to expand. The expansion of the fluid absorbing particles 146 causes the bladder 136 to inflate and form the shape shown in FIG. 7. The shape of the spinal support member 104 may conform to the patient when the spinal support member 104 is adhered to the patient via the double sided adhesive 150. In that way, when the spinal support member 104 is adhered to the patient and is inflated, the patient and the attached spinal support member 104 may be positioned on the base member 102 of the spinal immobilization device 100 such that the spinal support member 104 fits within the channel 114 formed within the top surface 110 of the base member 102. The patient and spinal immobilization device 100 may then be transported or further supported on a cot, stretcher, gurney, or other transportation device.

The bladder 136 of the spinal support member 104 may be constructed of an elastic or inelastic material. In certain instances, the bladder 136 of the spinal support member 104 may be constructed of latex, polyurethane, or the like.

Figure 11:
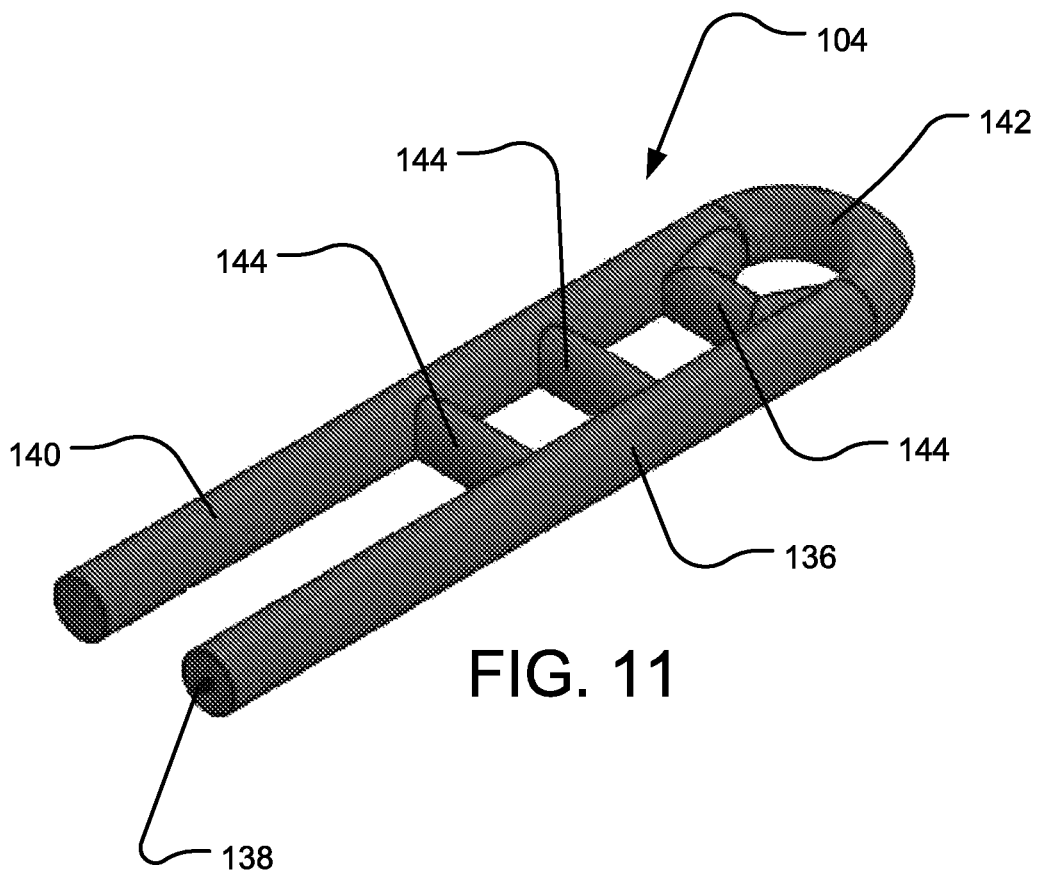
FIG. 11 is an isometric top view of another spinal support member as viewed from the foot end.
Figure 12:
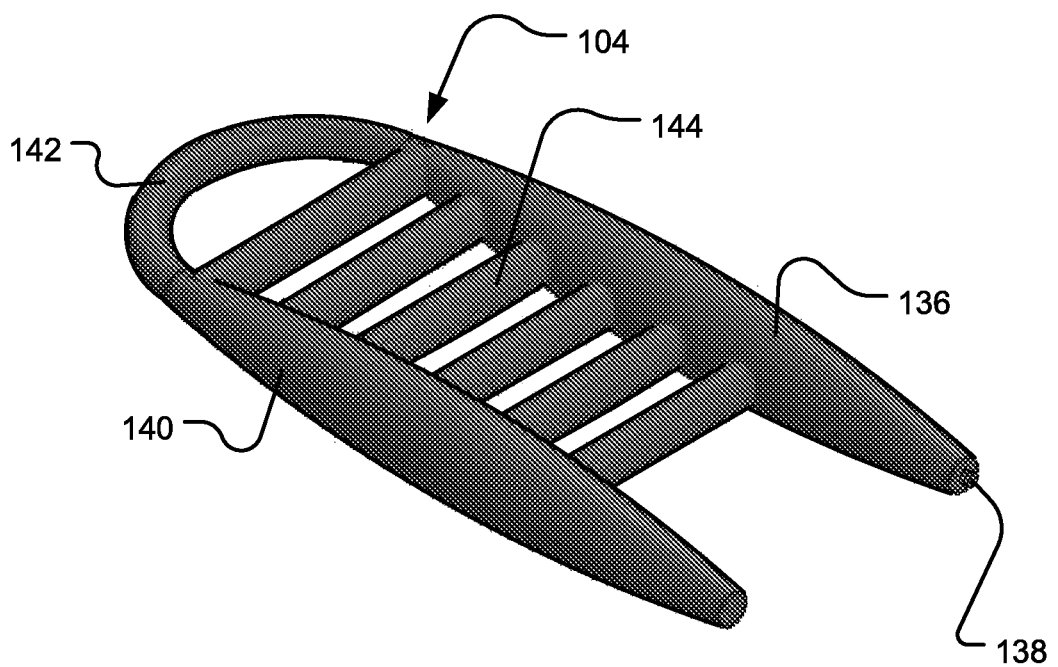
FIG. 12 is an isometric top view of another spinal support member as viewed from the foot end.

FIGS. 11 and 12 are isometric views of spinal support members 104 in various instances. FIG. 11 illustrates a spinal support member 104 from a foot end thereof. The spinal support member 104 is similar to the design shown in FIGS. 7-10, except the superior most transverse support member 144 may be curved or angled so as to generally define a circle with the head support member 142.

FIG. 12 illustrates a spinal support member 104 from a foot end thereof. As with the spinal support member of FIGS. 7-10, it includes a pair of longitudinal member 140, a curvate head support member 142, and transverse support members 144 interconnecting the longitudinal support members 140. The support member 104 in FIG. 12, however, includes bulbous longitudinal support members 140. In particular, the longitudinal support members 140 include enlarged mid-sections that are larger in circumference than the respective ends of the members 140. Also, there are six transverse support members 144 interconnecting the longitudinal support members 140 so as to support a patient's spine in a consistent, spaced-apart fashion. Whereas the transverse support members 140 in FIGS. 7-9 are designed and spaced apart to fit specific areas of a patient's spine, the spinal support member 104 in FIG. may be designed to provide a constant support surface with evenly spaced-apart members 144. While FIG. 12 depicts six transverse support members 144, the spinal support member 104 may include more or less support members 144 without departing from the scope of the disclosure.

Figure 13:
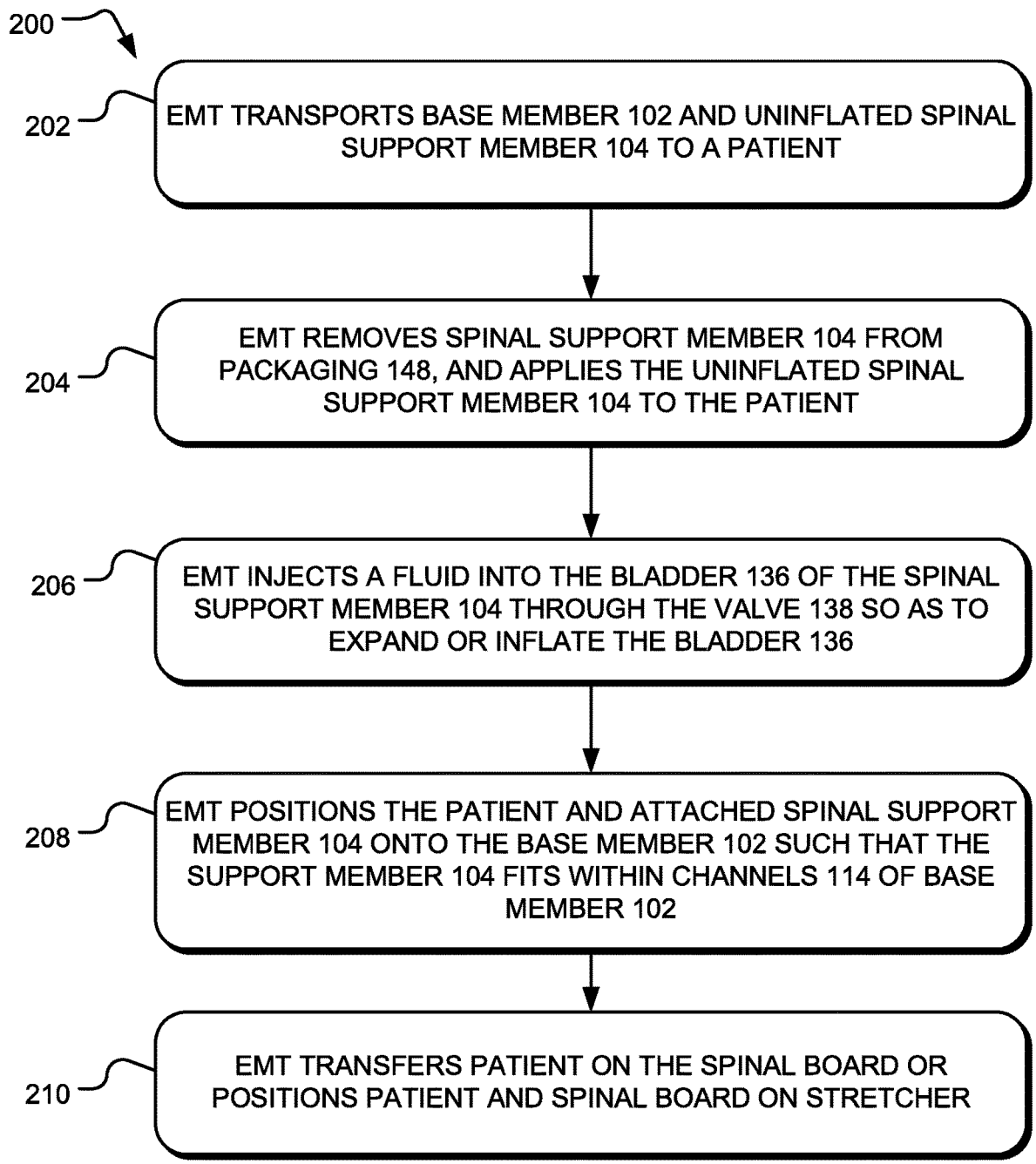
FIG. 13 is a flowchart showing an exemplary method of utilizing the spinal board.

An exemplary method 200 of using the spinal immobilization device 100 may be as follows, as illustrated in the flowchart of FIG. 13. At step 202, an EMT may transport a base member 102 and an uninflated spinal support member 104 to a patient in need of immobilization. At step 204, the EMT may remove the spinal support member 104 from the packaging 148, and apply the uninflated spinal support member 104 to the patient. This step may entail removing double-sided tape 150 from the spinal support member 104 and adhering the spinal support member 104 to the patient via the tape 150. At step 206, the EMT may inject a fluid (e.g., saline, water) into the bladder 136 of the spinal support member 104 through the valve 138 with a sufficient amount of fluid to expand the fluid absorbing members 146. This causes the bladder 136 to expand/inflate and conform to the unique and variable position of the patient, who may be unable to safely move without immobilization. At step 208, the EMT may position the patient, with the attached spinal support member 104 in an inflated state, on the base member 102 such that the spinal support member 104 fits within the channels 114 formed within the top surface 110 of the base member 102. At step 210, the patient, supported on the base member 102 and immobilized by the spinal support member 104, may be transported to a cot, stretcher, or gurney, or may be transported on the base member 102. The patient may additionally or alternatively be secured to the base member via straps.

Figure 14:
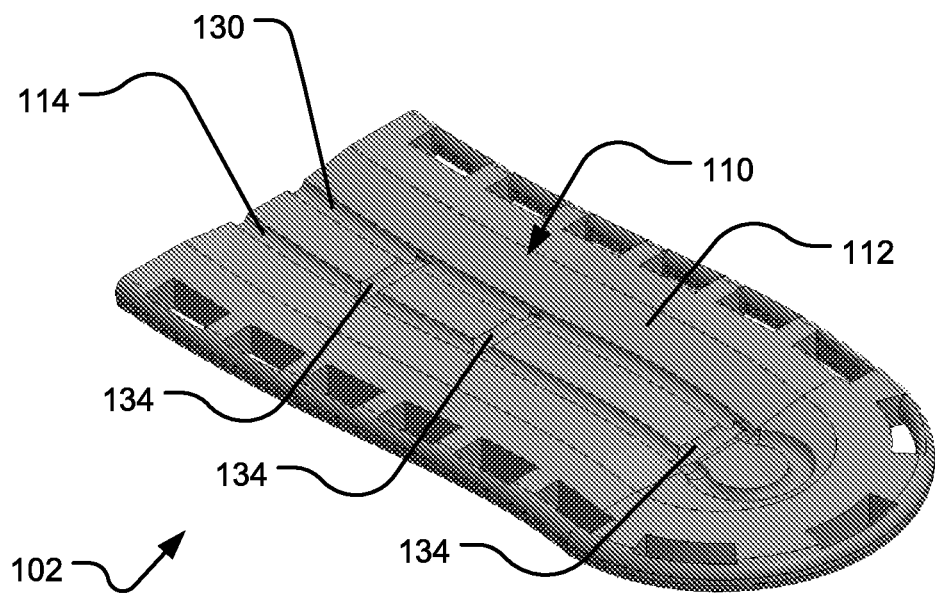
FIG. 14 is an isometric top view of a base member of the spinal board as viewed from the head end.
Figure 15:
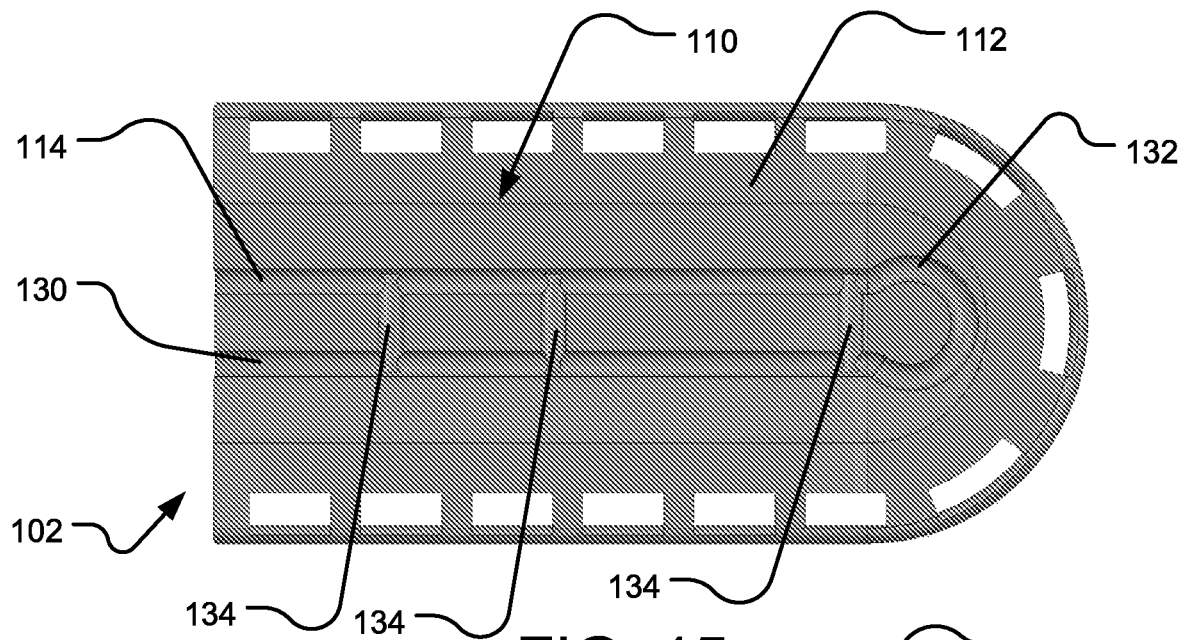
FIG. 15 is a top view of the base member.
Figure 16:
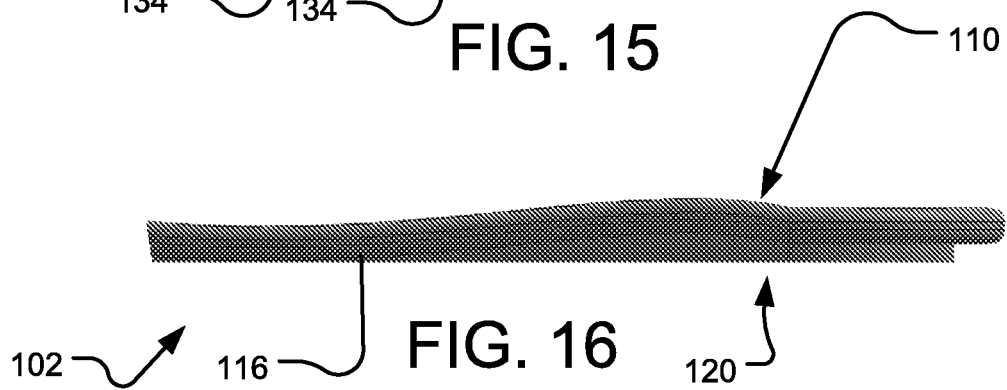
FIG. 16 is a side view of the base member.

FIGS. 14-16 depict a base member 102 that may include many of the elements as previously described. In certain instances, the base member 102 of FIGS. 14-16 may include a channel 114 formed in the curvate top surface 112 of the elongate board 110 that is different than previously described. The pair of spinal support sections 130 are closer together in the base member 102 of FIGS. 14-16, the transverse sections 134 are irregularly spaced-apart from each other, and the head support section 132 of the channel 114 is more circular. The channel 114 is designed to receive the spinal support member 104 of FIGS. 17-18 therein.

Figure 17:
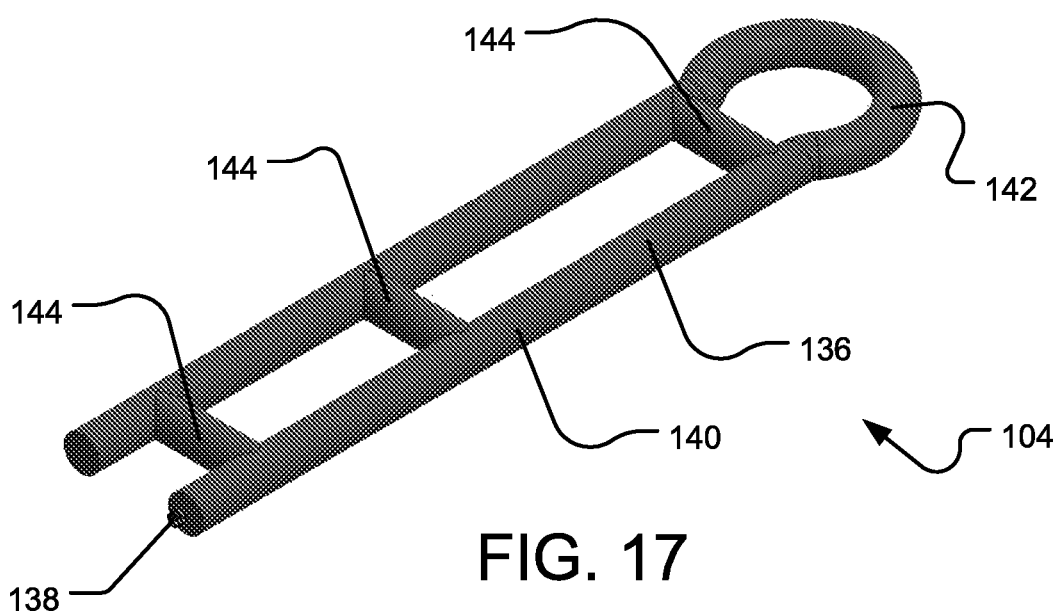
FIG. 17 is an isometric top view of a spinal support member as viewed from the foot end, where the spinal support member is in an expanded or inflated state with a single fill valve.
Figure 18:
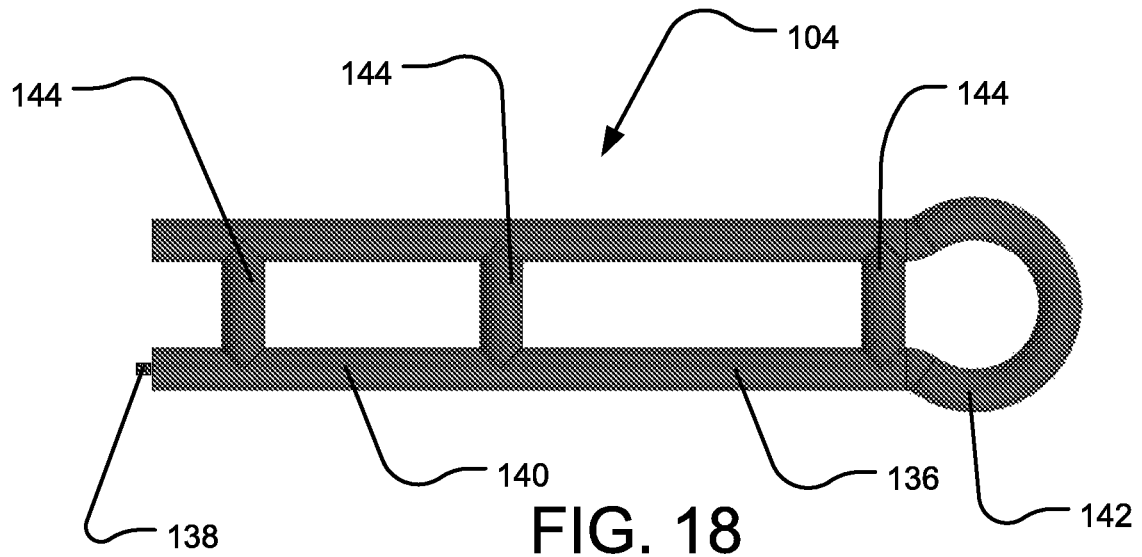
FIG. 18 is a top view of the spinal support member in the expanded or inflated state with a single fill valve.

As seen in FIGS. 17-18, the longitudinal support members 140 are closer together as compared to the previously described instances of the spinal support member 140. The longitudinal support member 140 are spaced-apart so as to support opposite sides of the spinal column of a patient. That is, the longitudinal support members 140 are designed to fit snugly against the spinal column so as to immobilize it upon inflation.

The head support member 142 is nearly a complete circular perimeter. It forms a full circumference of the head of a patient in combination with the first transverse support member 144. The patient's head is to be supported in a full circle or donut such that the head support member 142 and the first transverse support member 144 form a circle with a diameter of about 7.5 inches to about 8 inches. The first transverse support member 144 is positioned so as to support the patient between vertebraes C3 and C7. The second or intermediate transverse support member 144 is positioned to support the patient at the lumbar spine, and the third transverse support member 144 is positioned to support the patient at the coccyx or tailbone. An overall length of the spinal support member 104 may be about 36 inches.

The spinal support member 104 in FIGS. 17-18 includes a single valve 138 for filling the bladder 136. In this instance, the single valve 138 is positioned at a terminal end of one of the longitudinal support members 140.

Figure 19:
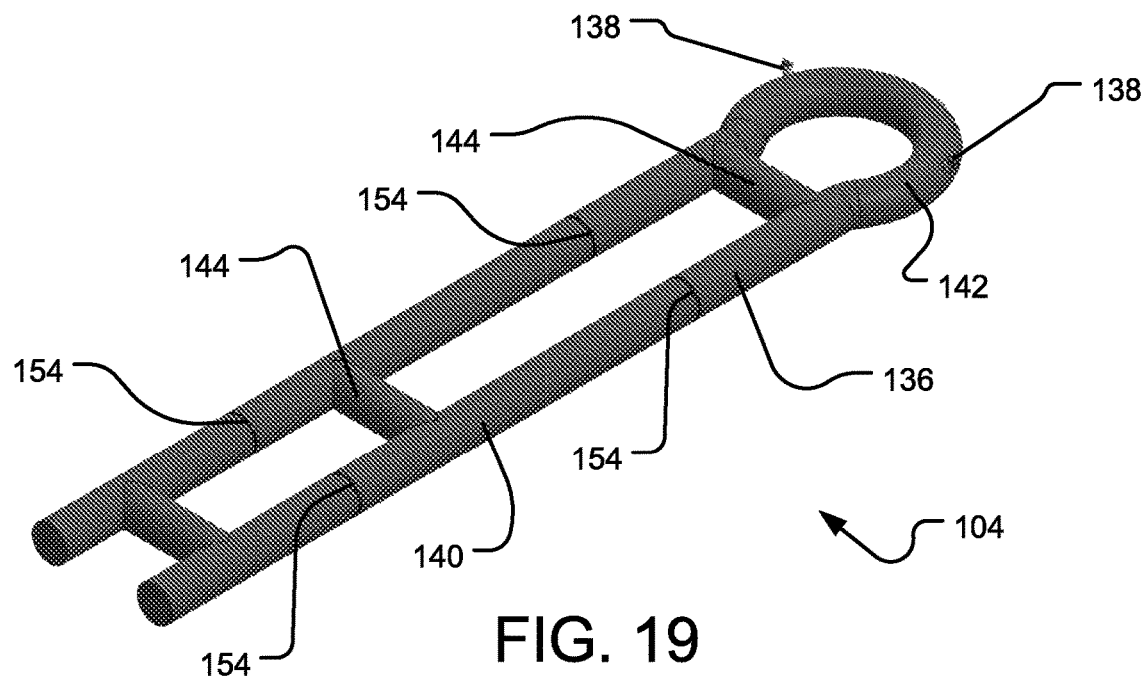
FIG. 19 is an isometric top view of a spinal support member as viewed from the foot end, where the spinal support member is in an expanded or inflated state with a pair of fill valves.
Figure 20:
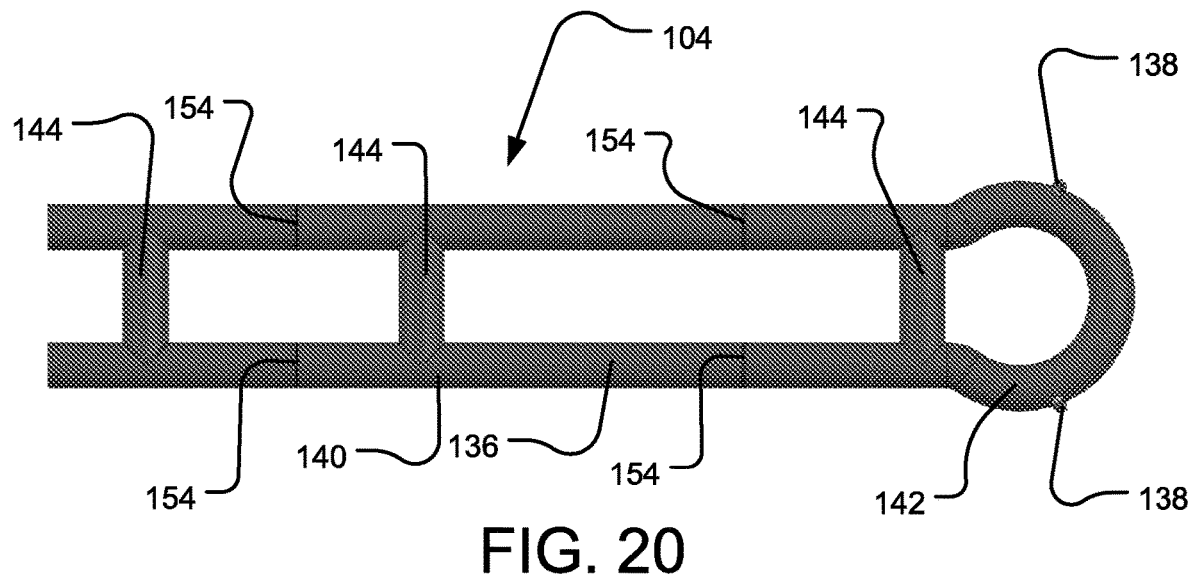
FIG. 20 is a top view of the spinal support member in the expanded or inflated state with a pair of fill valves.

As seen in FIGS. 19-20, the longitudinal support members 140 are closer together like the members 140 in FIGS. 17-18. The longitudinal support member 140 are spaced-apart so as to support opposite sides of the spinal column of a patient. That is, the longitudinal support members 140 are designed to fit snugly against the spinal column so as to immobilize it upon inflation.

The head support member 142 is nearly a complete circular perimeter. It forms a full circumference of the head of a patient in combination with the first transverse support member 144. The patient's head is to be supported in a full circle or donut such that the head support member 142 and the first transverse support member 144 form a circle with a diameter of about 7.5 inches to about 8 inches. The first transverse support member 144 is positioned so as to support the patient between vertebraes C3 and C7. The second or intermediate transverse support member 144 is positioned to support the patient at the lumbar spine, and the third transverse support member 144 is positioned to support the patient at the coccyx or tailbone. An overall length of the spinal support member 104 may be about 36 inches.

The spinal support member 104 in FIGS. 19-20 includes a pair of valves 138 for filling the bladder 136. In this instance, the valves 138 are positioned on opposite portions of the head support member 142, near where the ears of the patient would be located when the spinal support member 104 supports a patient. As seen in FIGS. 19-20, the spinal support member 104 may include internal baffles 154 within the bladder 136 to keep the fluid absorbing particles 146 within a particular section of the bladder 136. The baffles 154 may permit fluid to pass through, but not the fluid absorbing particles 146. The baffles may be a screen or mesh material that prevents the fluid absorbing particles 146 from migrating within the bladder 136. As seen in FIGS. 19-20, there are two baffles 154 on each of the longitudinal support members 140. Thus, the spinal support member 104 includes four internal baffles 154. In certain instances, the baffles 154 may be evenly spaced such that the total volume of fluid absorbing particles 146 is even distributed within the divided sections fo the spinal support member 104.

While the present disclosure has been described with reference to various implementations, it will be understood that these implementations are illustrative and that the scope of the present disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

In general, while the embodiments described herein have been described with reference to particular embodiments, modifications can be made thereto without departing from the spirit and scope of the disclosure. Note also that the term "including" as used herein is intended to be inclusive, i.e. "including but not limited to."

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

What is claimed is:

1. A spinal immobilization device comprising:

A base member and a spinal support member configured to overlay the base member, the base member comprising an elongate board having a curvate top surface, a plurality of openings surrounding at least a portion of the elongate board, and a channel defined within the top surface, the spinal support member comprising a bladder, at least one valve controlling passage of fluid into and out of the bladder, and a plurality of fluid absorbing members within the bladder, the channel defining an impression within the top surface that matches a shape of a portion of the bladder, wherein the bladder comprising a head support portion and a spinal support portion, and the channel comprising a head support portion and a spinal support portion, the head support portion and the spinal support portion of the bladder configured to partially inlay within the head support portion and the spinal support portion of the channel, respectively.

2. The spinal immobilization device of claim 1, wherein the spinal support portion of the bladder comprises a pair of tubular structures, and the head support portion of the bladder comprises a semi-circular tubular structure that interconnects the pair of tubular structures at an end thereof.

3. The spinal immobilization device of claim 2, wherein the bladder further comprises a plurality of tubular support structures coupled between the pair of tubular structures.

4. A spinal immobilization device comprising:

A base member, a spinal support member configured to overlay the base member, and a double-sided adhesive, the base member comprising an elongate board having a curvate top surface, a plurality of openings surrounding at least a portion of the elongate board, and a channel defined within the top surface, the spinal support member comprising a bladder, at least one valve controlling passage of fluid into and out of the bladder, and a plurality of fluid absorbing members within the bladder, the channel defining an impression within the top surface that matches a shape of a portion of the bladder, the double-sided adhesive adhered to the bladder on one side of the double-sided adhesive.

5. A spinal immobilization device comprising:

A base member and a spinal support member configured to overlay the base member, the base member comprising an elongate board having a curvate top surface, a plurality of openings surrounding at least a portion of the elongate board, and a channel defined within the top surface, the spinal support member comprising a bladder, at least one valve controlling passage of fluid into and out of the bladder, a plurality of fluid absorbing members within the bladder, and at least one baffle positioned within the bladder to restrain movement of the plurality of fluid absorbing members within the bladder, the channel defining an impression within the top surface that matches a shape of a portion of the bladder.

6. The spinal immobilization device of claim 5, wherein the at least one baffle permits fluid to pass there through.

7. A method of immobilizing a spine of a patient having a head, the method comprising:

applying a spinal support member of a spinal immobilization device to the spine of the patient, the spinal support member comprising a bladder, at least one valve controlling passage of fluid into and out of the bladder, and a plurality of fluid absorbing members within the bladder, the bladder being uninflated when the spinal support member is applied to the spine of the patient;

injecting a fluid into the bladder of the spinal support member through the at least one valve, thereby causing the plurality of fluid absorbing members to expand whereby inflating the bladder; and positioning the patient on a base member of the spinal immobilization device such that the spinal support member fit within channels formed in a top surface of the base member.

8. The method of claim 7, wherein applying the spinal support member to the spine of the patient comprises taping the spinal support member to the spine of the patient.

9. The method of claim 7, wherein the spinal support member comprises a semi-circular head support portion coupled to a pair of longitudinal support members, the semi-circular head support portion configured to support the head of the patient, the pair of longitudinal support members configured to support sides of the spine of the patient.

10. The method of claim 7, further comprising removing the spinal support member from packaging prior to applying the spinal support member to the spine of the patient.

11. The method of claim 7, further comprising transferring the patient on the base member to a stretcher.

* * * * *